United States Patent [19]

Smith, Jr. et al.

[11] Patent Number: 5,173,209
[45] Date of Patent: Dec. 22, 1992

[54] STABLE LITHIUM CYCLOALKYLIMIDES

[75] Inventors: W. Novis Smith, Jr.; Christopher Louer, both of Philadelphia, Pa.

[73] Assignee: Cyprus Foote Mineral Company, Malvern, Pa.

[21] Appl. No.: 581,900

[22] Filed: Sep. 13, 1990

Related U.S. Application Data

[63] Continuation-in-part of Ser. No. 374,740, Jun. 30, 1990, and a continuation-in-part of Ser. No. 521,743, May 10, 1990, Pat. No. 5,068,368.

[51] Int. Cl.$^5$ ................................................ C09K 3/00
[52] U.S. Cl. ............................ 252/182.14; 252/182.12
[58] Field of Search ....................... 252/182.14, 182.12

[56] References Cited

U.S. PATENT DOCUMENTS

| | | | |
|---|---|---|---|
| 4,051,066 | 9/1977 | Miksic et al. | 252/389 R |
| 4,895,841 | 1/1990 | Sugitomo et al | 514/212 |
| 4,910,304 | 3/1990 | Fischer et al. | 540/612 |
| 4,958,024 | 9/1990 | Miyano et al. | 546/249 |
| 5,068,368 | 11/1991 | Smith et al. | 552/556 |

OTHER PUBLICATIONS

Fuchigami et al.. *Chem. Abs.*, 104, p. 702, abs. #109392w (1986).
Dmowski, *Chem. Abs.*, 102, p. 581, abs. #62044a, (1985).

*Primary Examiner*—Edward A. Miller
*Attorney, Agent, or Firm*—John Lezdey

[57] ABSTRACT

A composition of at least one lithium cycloalkyl imide of the formula:

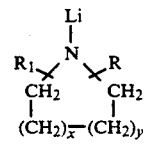

wherein R and R′ each represent a hydrogen or alkyl of 1 to 4 carbon atoms, and x and y are integers of 1 to 3.

4 Claims, No Drawings

STABLE LITHIUM CYCLOALKYLIMIDES

RELATED APPLICATIONS

This application is a continuation-in-part application of application Ser. No. 374,740 filed Jun. 30, 1990, entitled "Stable Lithium Amides and Reagent Compositions Thereof" and of application Ser. No. 521,743, filed May 10, 1990, entitled "Stabilized Lithium Acetylide and Reactions Therewith" of Smith et al., now U.S. Pat. No. 5,068,368.

FIELD OF THE INVENTION

The present invention relates to stable lithium cycloalkylimides and reagent compositions which comprise these compounds. More particularly, the invention concerns the preparation of stable solutions of lithium cycloalkylimides and to reagent compositions thereof containing increased concentrations of the lithium cycloalkylimides in solution. The reagent compositions are capable of producing increased yields in subsequent reactions such as the formation of lithium acetylide which may be used in simultaneous or subsequent reactions with aldehydes and ketones, and the direct metalation of ketones followed by subsequent reactions.

BACKGROUND OF THE INVENTION

Lithium amides, for example, lithium diisopropylamide, are widely used as reagents for reactions with aldehydes and ketones in the preparation of pharmaceuticals and specialty chemicals. Lithium amides are particularly useful for the preparation of lithium acetylide compounds which are used to form acetylenic substituted organic compounds such as steroid and fragrance intermediates. In order to form the lithium acetylide, acetylene is reacted with a lithium amide, such as lithium diisopropylamide just prior to reacting the newly formed lithium acetylide with the ketone or other reagent in the same reactor. All of the steps in the prior art are performed below 0°C. Usually, it is necessary to add an ether cosolvent such as tetrahydrofuran (THF) at this point to increase the limited solubility of the reagents and the subsequently formed lithium salt of the product from the reaction with the ketone. The lithium amide may be added as a preformed solution or it may be formed in the same reactor by reacting an alkyllithium such as n-butyllithium with an amine such as diisopropyl amine. In either case, the lithium amide usually exhibits lower solubility than desired for maximum reactivity and yet there is a need to minimize the amount of solvents employed.

In order to increase the concentration of the lithium amide in the preformed solutions, ethers such as tetrahydrofuran and/or complexing agents such as organomagnesium compounds, which are also stabilizing agents, have been added to increase the solubility of the lithium amide in solution. The presence of the ethers makes these solutions unstable and they decompose on standing in storage. The presence of magnesium compounds in the reaction and subsequent workup is undesirable because the possibility of lower reactivity and yields of desired products plus the more difficult workup due to the presence of the formed magnesium oxide and hydroxide which are highly insoluble and formed during washing.

Additionally, when tetrahydrofuran is used as the solvent it has been found necessary to limit the amount of tetrahydrofuran to no more than one mole for each mole of lithium amide in order to minimize degradation of the system. This also produces problems in recovering mixed solvents.

Aromatic solvents were not utilized as the solvent for preparing preformed lithium amide solutions in the past because the increased solubility was not appreciated and the belief that there would result a degradation of the organo lithium in an aromatic solution. It has been found that mixed amines provide higher solubilities in alyshatis solvents.

Monolithium acetylide is a valuable reagent for the preparation of ethynyl carbinols and terminal acetylenes. Monolithium acetylide has been used to ethynylate 17-keto steroids unsubstituted in the $C_{16}$ position. However, it was previously necessary to utilize only tetrahydrofuran (THF) or other ethereal solvents to prepare the reagent. Such solvents cause problems in commercial scale processes.

It is well known to prepare 17-keto, 3-keto or 3, 17-diketo steroids with substituents on the A, B or C rings, see for example U.S. Pat. Nos. 3,166,551; 3,065,146; 3,516,991; 3,629,298 and 4,216,159.

M. M. Midland in J. Org. Chem. 40, 2250 (1975) reported reacting n-butyllithium with acetylene in THF at low temperatures ($< -70°$ C.) and in dilute solutions to produce monolithium acetylide. (See Fieser and Fieser, Reagents for Organic Synthesis, Vol. 1, Wiley, New York, 1967, p. 573). Midland found that warming or attempting to generate a more concentrated solution resulted in disproportionation to the insoluble dilithium acetylide and acetylene. This disproportionation is an important disadvantage and occurs in the absence of a complexing agent. (See Corbellini et al, Chem. Ind. (Milan) 42, 251 (1960) and Chem. Abstr. 54, 19250 (1960)). To reduce or prevent the disproportionation, the monolithium acetylide is usually prepared in liquid ammonia, which presumably services as an appropriate complexing agent. An amine such as ethylenediamine can also be used to stabilize monolithium acetylide. Ethylenediamine, while stabilizing monolithium acetylide to the point it can be sold commercially, actually reduces the reactivity of the reagent to the point that it is not useful for many ethynylation procedures.

U.S. Pat. No. 4,005,562 discloses the use of monolithium acetylide to ethynylate 17-keto steroids unsubstituted in the $C_{16}$ position. The monolithium acetylide was prepared by bubbling acetylene into THF held at $-70°$ C. under anhydrous conditions followed by addition of butyllithium. The 17-keto steroid was added to the unstabilized monolithium acetylide and the mixture stirred for 3 hours at $-70°$ C. to produce the 17$\alpha$-ethynyl-17$\beta$-hydroxy steroid product.

U.S. Pat. No. 4,320,236 discloses the use of a monolithium acetylide-ammonium complex (which is well known to those skilled in the art) to ethynylate ketones at below about $-30°$ C. The examples in U.S. Pat. No. 4,320,236 disclose ethynylation reaction temperatures of $-50°$ to $10°$ C. The unsaturated acyclic ketones ethynylated in U.S. Pat. No. 4,320,236 are very reactive whereas the monolithium acetylide reagent produced by the process of the present invention is reactive with steroidal 17-ketones such as cyclopentanones, that are ordinarily much less reactive.

U.S. Pat. No. 4,526,720 to Van Rheenen et al discloses a one pot and a two pot process for preparing monolithium acetylide. Each reaction involves contacting an organolithium compound with a solution containing acetylene in the presence of a stabilizing amine. The amine reacts with the organolithium compound to form a lithium complex and/or a corresponding lithium amide which is subsequently reacted with acetylene.

U.S. Pat. No. 4,595,779 to Morrison et al relates to a composition and method for preparing lithium diisopropylamide by the reaction of lithium metal and diisopropylamine in tetrahydrofuran and an inert liquid hydrocarbon cosolvent including styrene as an electron carrier. However, the use of tetrahydrofuran is considered essential in the preparation when utilizing lithium metal.

The article of Keith Smith entitled "Lithiation and Organic Synthesis", *Chemistry In Britain.* Jan. 1982, pages 29-32, discloses the preparation of lithium dialkyl amides for use as lithiating agents by the reaction of organolithium reagents in aliphatic hydrocarbon solvents.

U.S. Pat. No. 3,542,512 to Honeycutt relates to the preparation of lithium amide by contacting lithium metal with liquid ammonia and then heating the mixture at a temperature about 150° degrees C. in an inert liquid medium. The inert liquid medium includes aromatic compounds having a boiling point above 200 degrees C.

It is an object of the present invention to provide novel lithium cycloalkylimides reagent compositions having greater amounts of the lithium cycloalkylimides in solution.

It is a further object of the invention to provide a process for preparing lithium cycloalkylimides in higher concentrations in solution and in a solvent which is stable.

It is a yet still further object of the invention to prepare lithium cycloalkylimides in situ to utilize the resulting mixture to prepare lithium acetylide and optionally carry on further reactions with aldehydes or ketones.

It is still another object of the invention to prepare novel lithium cyclohexamethylenimine and reagent compositions thereof.

It is yet another object of the invention to provide a novel mixture of lithium compounds for use in a reagent composition for the preparation of lithium acetylide in high yields.

SUMMARY OF THE INVENTION

In accordance with one embodiment of the invention it has been found that soluble lithium cycloalkylimides could be prepared in high concentrations by the reaction of in a suitable an alkyl lithium compound with a cycloalkylimine in a suitable organic solvent.

More particularly, the invention is concerned with the preparation of lithium cycloalkylimides by the step of reacting an alkyl lithium compound of 1 to 8 carbon atoms with an imine of the formula:

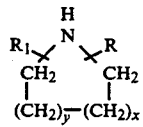

wherein R and $R_1$ are each selected from the group consisting of hydrogen and alkyl of 1 to 4 carbon atoms, and x and y are each an integer of 1 to 3.

In accordance with another embodiment of the invention there is prepared lithium acetylide by the use of at least one lithium cycloalkylimine in a solvent, preferably comprising an aromatic hydrocarbon, in a reaction with acetylene.

In a still further embodiment of the invention, the lithium acetylide is reacted simultaneously or subsequently with a carbonyl-containing compound, such as an aldehyde or ketone to form the corresponding hydroxyl carbonyl compound. The reactions can all take place in the same reaction vessel with a suitable solvent for subsequent reactions without the need of any ethers, extra amines or stabilizers other than those formed from the lithium cycloalkylimine.

Surprisingly, the reaction to form the carbonyl compounds may be at higher temperatures, for example, at ambient temperatures, preferably between 0° and 20° C. when prepared in an aromatic solvent.

The reactions involved in the processes of the invention are as follows:

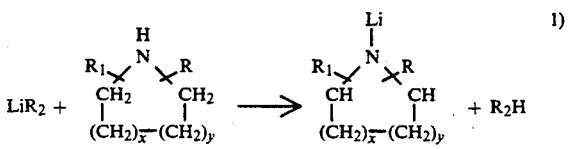

wherein $R_2$ is an alkyl group of 1 to 8 carbon atoms, and R, $R_1$, x and y are as hereinbefore, defined.

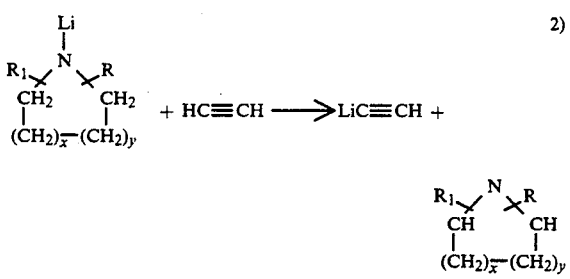

wherein R, $R_1$ x and y are as hereinbefore defined,

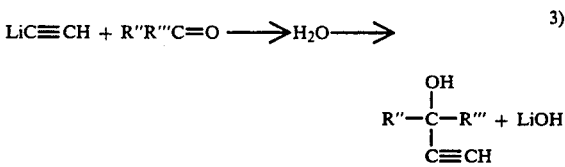

wherein R" can be hydrogen or lower alkyl ($C_1$-$C_4$), R''' can be hydrogen, or any aliphatic, alicyclic or aromatic hydrocarbon group which can be unsubstituted or substituted, or R" and R''' together with the carbon to which they are attached is a steroid.

The hydrolysis of the ethynyl compound can be effected in a known manner, e.g., with dilute sulfuric acid, acetic acid, water, ammonium chloride, and the like to form the corresponding ethynyl carbinol.

DETAILED DESCRIPTION OF THE PREFERRED EMBODIMENTS

The present invention is concerned with novel lithium cycloalkylimides, lithium, dimethylaminopropylamide, reagent compositions containing these compounds, and similar compounds, their use in the preparation ethynyl carbinol compounds, and for direct metalation reactions.

More particularly, the invention relates to a lithium cycloalkylimine of the formula:

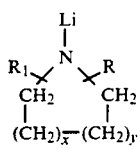

wherein $R_1$ and $R_2$ are each hydrogen or alkyl of 1 to 4 carbon atoms, and x and y are each an integer of 1 to 3. The most preferred compound is lithium hexamethyleneimide. These compounds possess high solubility in most organic solvents. However, they are most advantageously utilized in an aromatic solvent. The compounds can be used alone or in combination with a lithium dialkylamide such as lithium dimethylaminopropylamide to prepare lithium acetylide without isolation.

The same reaction mixture can be used for subsequent reactions with aldehydes and ketones which after hydrolysis yields a compound of the formula:

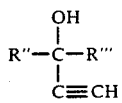

wherein R" is hydrogen or lower alkyl ($C_1$-$C_4$). R'" is hydrogen, or any aliphatic, alicyclic or aromatic hydrocarbon group which is unsubstituted or substituted, or R" and R'" together with the carbon to which they are attached is a steroid.

Among the preferred groups are alkyl, alkenyl, alkynyl, cycloalkyl, cycloalkenyl, aryl, aryl-lower alkyl, aryl-lower alkenyl, cycloalkyl-lower alkyl and cycloalkenyl-lower alkenyl.

In accordance with another embodiment of the invention, the aforementioned aryl, cycloalkyl or cycloalkenyl groups can be unsubstituted or substituted in at least one position with one or more substituents selected from the group consisting of lower alkyl, lower alkoxy, halo, trifluoromethyl, amino, hydroxyl and carboxyl.

The term "aliphatic hydrocarbon" includes open chain aliphatic and cycloaliphatic hydrocarbons as well as hydrocarbons containing both aliphatic and cycloaliphatic moieties.

The term alkenyl designates alkenyl groups having at least one olefinic double bond and containing from 2 to 20 carbon atoms such as vinyl, allyl, 5-octenyl, 2,3-dimethyl-4-octenyl, 8-hexadecenyl, 5,6-dimethyl-7-hexadecenyl, 5,6-dimethyl-7-hexadecenyl, etc. The term alkynyl includes alkynyl groups having at least one triple bond and containing from 3 to 20 carbon atoms such as propynyl, 3,7-dimethyl-5-octynyl, 6-heptadecynyl, etc.

Cycloalkyl groups which are designated by R" and R'" generally contain from 3 to 8 carbon atoms, such as cyclopropyl, cyclohexyl and the like. The cycloalkenyl groups contain from 3 to 8 carbon atoms, such as cyclopropenyl, cyclohexenyl, etc. The term "aryl" includes aromatic, monocyclic or bicyclic residues which can, if desired, contain a hetero atom in the ring. Among the preferred hetero atoms are sulfur, oxygen and nitrogen. The preferred aromatic residues are phenyl, naphthyl, pyridinyl, and the like.

The term "lower alkyl" includes saturated aliphatic hydrocarbon radicals containing from 1 to 7 carbon atoms such as methyl, ethyl, n-propyl, isopropyl, etc. The term "lower alkenyl" designates lower alkenyl radicals containing from 2 to 7 carbon atoms such as vinyl, allyl, etc. The term "lower alkoxy" includes lower alkoxy radicals containing from 1 to 7 carbon atoms such as methoxy, isopropoxy, ethoxy, etc.

The aromatic solvents which may be used in the present invention include benzene, toluene, ethyl benzene, cumene, xylene diisopropyl benzene, and the like.

Other solvent hydrocarbons such as cycloalkanes, more particularly, cyclopentane, cyclohexane, or the like, or aliphatic hydrocarbons such as hexane, heptane, or the like. It is also understood that tetrahydrofuran and other ethers may be used or added to the solvent, although, this is not preferred. The solvents may be used alone or in admixture with each other. A preferred mixture is toluene and cyclohexane.

Advantageously, the reactions to prepare the lithium acetylide and the subsequent reactions can be performed in the same reaction vessel without separation and in the same solvent. It is well known that allowing the monolithium acetylide to stand even at $-78°$ C. for 6 hours with an atmosphere of acetylene may lower the yield 10%. In the past, a stabilizing amine was utilized to form a complex with the monolithium acetylide but the additional amine is not necessary in the present invention. Also, the presence of mixed solvents as proposed in the prior art is not essential since it makes recovery of the solvent and the product after each reaction more difficult.

Examples of suitable compounds which may be used in the invention to prepare the corresponding ethynylcarbinol include:

| | |
|---|---|
| Cyclopentanone | Acetaldehyde |
| Cyclohexanone | 4-Androstene-3,17-dione |
| Cycloheptanone | 4-Androstene-17-one |
| Acetone | Isophorone |
| 2-Butanone | Mesityl oxide |
| 3-Pentanone | Benzal acetone |
| Fenchone | Dibenzal acetone |
| 2- or 3-Octanone | Acetophenone |
| Diisopropyl ketone | Propiophenone |
| 2-Cyclohexylcyclohexanone | Benzophenone |
| 3-Cyclohexylcyclohexanone | 9-Fluorenone |
| Benzaldehyde | 1-Indanone |
| | Tetralone |

In accordance with another embodiment of the invention, there is provided novel catalysts and reagent compositions comprising at least one lithium cycloalkylimide of the formula:

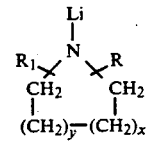

wherein R and $R_1$ are each selected from the group consisting of hydrogen and alkyl of 1 to 4 carbon atoms, and x and y are each an integer of 1 to 3.

The reagent compositions which comprise the lithium cycloalkyl imides of the invention in a solvent can include lithium amides such as disclosed in application Ser. No. 374,740, namely, the lithium amides derived from alkyl amines such as methyl amine, isopropyl amine, isoamylamine and the like, dialkyl amines such as dimethyl amine, diethylamine, diisopropyl amine, diisobutyl amine, diisoamyl amine, dialkyl heptylamine, dialkylhexyl amine, for example, dimethylhexylamine and diethyl hexyl amine, N, N'-dialkyl alkylene diamine, for example, N, N'-di(tert-butyl)ethylene diamine, N, N-dimethylaminoethyl amine, N, N-dimethyl aminopropyl amine, N, N, N'-trimethylethylene diamine, N, N-dipropylaminopropylene amine, N, N'-diethyl -1, 3-propanediamine, N, N, N'-trimethylethylene diamine, N, N, N'-triethylethylene diamine, N, N-dimethyl-N'-ethylethylene diamine and the like.

The preferred amines which may be utilized in admixture with the imides of the invention include dimethylaminopropyl amine (DMAPA), diethylaminoethyl amine, diisoamyl amine, diisobutyl amine, di-sec-butylamine, diisopropyl amine and diethylhexylamine.

It has been surprisingly discovered that the preparation of a reagent composition of lithium cycloalkylimides which includes lithium amides increases the solubility of the amides especially in an aromatic solvent. Also, the preparation of an ordinarily insoluble lithium amide together with a soluble lithium cycloalkyl imide results in the solubility of said otherwise less soluble lithium amide.

The principal advantage of the lithium cycloalkyl imides of the invention is their high solubility in most solvents. This feature permits the selection of a solvent which can be used in a continuous process. Furthermore, when used or prepared in combination with a lithium amide in an aromatic solvent particularly, lithium dimethylaminopropyl amide, the reagent composition provides high yields even at ambient temperatures when used for ethynylation reactions.

Both lithium cycloalkyl imides and lithium dimethylaminopropyl amide have high solubility in most organic solvents.

The following examples are illustrative of the practice of the method of the present invention. It will be understood, however, that it is not to be construed as in any way limitative of the full scope of the invention since various changes can be made, without departing from the spirit of the teachings contained herein, in the light of the guiding principles which have been set forth above. All percentages herein stated are based on weight except wherein noted.

EXAMPLE 1

Preparation of Mixed Lithium Catalysts

To 20 ml. of n-butyl lithium (0.05M) in toluene is added 0.025 mole of dimethylaminopropylamine and 0.025 mole of hextamethylene imine in toluene. The mixture is stirred for 10 minutes. A 25% by weight reagent composition is formed containing a 50—50 mole ratio of mixed lithium reagents.

EXAMPLE 2

20.4 g (0.2 mole) of dimethylaminopropyl amine (DMAPA) were added to 100 ml (0.2 mole) of a 2.0M toluene solution of n-butyllithium under nitrogen with stirring at 20° C. The clear solution was cooled at 10° C. and saturated with acetylene (which was passed over alumina to remove acetone). The clear solution (the complex was totally soluble) was warmed up to 20° C. with stirring and bottled. After two weeks storage at room temperature, 0.18 moles of diisopropyl ketone in 50 ml toluene were added to this solution over a 30 minute period under nitrogen at 10° C. The solution was hydrolyzed with 20 ml water and then an anhydrous sodium sulfate was added. The solution was analyzed for ethynyl carbinol using gas chromatography with 1-octanol as the internal standard. The yield was 83%.

EXAMPLE 3

A. PREPARATION OF LITHIUM ACETYLIDE 12.6 g (0.2 mole) of hexamethyleneimine were added to 100 ml (0.2 mole) of a 1.6 M solution of n-butyllithium in toluene at 20° C. under nitrogen with stirring. The clear solution of the lithium hexamethyleneimide was then saturated with acetylene at 20° C. and stored. The lithium acetylide complex was soluble and stable.

The acetylene atmosphere was maintained while 17.1 g (0.15 moles) of diisopropyl ketone dissolved in 50 ml toluene were added at 30° C. over a one hour period. When the addition was completed, the solution was permitted to warm up over 30 minutes and then 20 ml of water were added. About 10–15 g of anhydrous sodium sulfate was added and the saturated salt layer allowed to settle. To this solution was then added 10.0 g 1-octanol and a sample of the solution injected into a gas chromatograph. The ratio of the peaks for product and the 1-octanol standard was corrected for response difference (1.1 times the 1-octanol peak). The yield of the ethynyl alcohol was 93%.

EXAMPLE 4

9.9 g (0.1 mole) of hexamethylenimine were added to 500 ml of a 2.1M (0.1 mole) solution of n-butyllithium in toluene at 20° under nitrogen. To this clear solution were added 0.1 mole of cyclohexanone and stirred for 0.5 hrs. Then 0.2 m of allyl bromide was added. The solution was hydrolyzed with 50 ml of water then anhydrous sodium sulfate. The clear organic layer was analyzed by gas chromatography for 2-propenyecyclohexanone. The yield was 95%.

The acetylene atmosphere was maintained while 17.1 g (0.15 moles) of diisopropyl ketone dissolved in 50 ml toluene were added at 30° C. over a one hour period. When the addition was completed, the solution was permitted to warm up over 30 minutes and then 20 ml of water were added. About 25 g of anhydrous sodium sulfate was added and the saturated salt layer allowed to settle. To this solution was then added 10.0 g 1-octanol and a sample of the solution injected into a gas chromatograph. The ratio of the peaks for product and the 1-octanol standard was corrected for response difference (1.1 times the 1-octanol peak). The yield of the ethynyl alcohol was 93%.

EXAMPLE 5

To demonstrate the increased solubility of the amides or imides of the invention the following experiments were performed. Molar equivalents of the corresponding imides and diamine were added to 2 ml of 15% n-butyllithium in the solvent under nitrogen. The addition was carefully performed with syringes and the glass bottle was then capped after the reaction subsided, about 2 minutes. The solutions were permitted to stand two weeks at 20 degrees C. with intermittent shaking to be certain crystals had equilibrated with the solution. 2 ml samples were taken and filtered and then injected into 25 ml water and titrated with 0.1 N HCl with adequate stirring. A pH meter was used to determine the end point of 7.0. There was no apparent break for the LiOH and the amine or diamine present. Therefore the total titration was divided by the equivalents of base present. For each mole of the amide formed, the titration would be divided by two for monoamines and three for diamines. Table 1 lists the results:

TABLE 1

| Alkyl amine | Solvent | Solubility |
| --- | --- | --- |
| A. hexamethyleneimine | cyclohexane | >1.6M |
|  | toluene | >2.2M |
|  | heptane | 0.7M |
| B. 90% dimethylaminopropyl amine 10% 2-diethylaminoethyl amine | toluene | >2.2M |
| C. hexamethyleneimine 20% diisopropyl amine 80% | cyclohexane | >1.6M |
| D. 3-methylpiperidine | toluene | 0.83M |
| E. dimethylaminopropyl amine | heptane | 1.1M |
| F. 20% hexamethyleneimine 80% diisobutylamine | heptane | >1.4M |
| G. diethylaminoethylamine | toluene | >2.2M |
|  | heptane | >1.4M |
| H. 90% hexamethyleneimine 10% diisobutylamine | toluene | >2.2M |
|  | heptane | 1.4M |

What is claimed is:

1. An ether-free reagent composition which comprises a lithium cycloalkylimide of the formula:

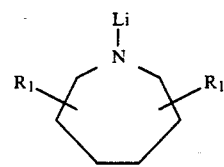

wherein R and $R_1$ are each selected from the group consisting hydrogen and alkyl of 1 to 4 carbon atoms, and
a hydrocarbon solvent, said reagent composition having a concentration greater than about 1.6 M.

2. The reagent composition of claim 1 wherein said solvent is selected from the group consisting of benzene, toluene, ethyl benzene, cumene, xylene and diisopropyl benzene.

3. The reagent composition of claim 1 wherein said solvent is selected from the group consisting of cyclopentane and cyclohexane.

4. The reagent composition of claim 1 wherein said lithium cycloalkylimide is lithium hexamethyleneimide.

* * * * *